United States Patent [19]
Cleary

[11] Patent Number: 6,133,483
[45] Date of Patent: Oct. 17, 2000

[54] PROCESS FOR THE PRODUCTION OF 2,4,4'-TRICHLORO-2'-METHOXYDIPHENYL ETHER

[76] Inventor: Thomas F. Cleary, 45451 S. Caspar Dr., Mendocino, Calif. 95460

[21] Appl. No.: 09/124,783

[22] Filed: Jul. 30, 1998

[51] Int. Cl.[7] .............................. C07C 43/29; C07C 41/01
[52] U.S. Cl. ............................................. 568/639; 568/637
[58] Field of Search ...................................... 568/637, 639

[56] References Cited

U.S. PATENT DOCUMENTS

| | | | |
|---|---|---|---|
| 3,506,720 | 4/1970 | Model | 568/637 |
| 4,467,117 | 8/1984 | Lund et al. | 568/637 |
| 4,486,610 | 12/1984 | Lund | 568/637 |

*Primary Examiner*—Michael G. Ambrose

[57] ABSTRACT

A process is disclosed for the synthesis of 2,4,4'-trichloro-2'-methoxydiphenyl ether, and it's precursor 2,4,4'-trichloro-2'-bromodiphenyl ether, a novel compound.

2 Claims, No Drawings

PROCESS FOR THE PRODUCTION OF 2,4,4'-TRICHLORO-2'-METHOXYDIPHENYL ETHER

CROSS REFERENCE TO RELATED APPLICATIONS

Not Applicable

STATEMENT REGARDING FEDERALLY SPONSERED RESEARCH OR DEVELOPMENT

Not Applicable

REFERENCE TO A MICROFICE APPENDIX

Not Applicable

FIELD OF INVENTION

This invention relates to a novel synthesis of 2,4,4'-trichloro-2'-methoxydiphenyl ether, useful as an intermediate in the preparation of 2,4,4'-trichloro-2'-hydroxy diphenyl ether, widely used in soap and cosmetics as a bactericidal agent, and known by the generic name Triclosan.

BACKGROUND OF THE INVENTION

From the time of its commerical introduction, Triclosan has been produced by a process consisting of the diazotization of 2,4,4'-trichloro-2'-aminodiphenyl ether with nitrosylsulfuric acid, followed by hydrolysis of the resulting diazonium bisulfate with hot, strong sulfuric acid. It is a disagreeable and wasteful aspect of this process that there is generated thereby a very substantial amount of an offensive co-product, 2,4,8-trichlorodibenzofuran. As a consequence it is necessary to separate this co-product from the formed Triclosan and to protect the environment by destroying it e.g., by incineration. Also, lengthy, expensive and rigorous purification procedures are needed to reduce the amount of this possibly hazardous substance to tolerable levels in Triclosan.

It is a practical objective therefore to produce Triclosan by a synthesis which does not generate 2,4,8-trichlorodibenzofuran as a co-product. Such a process has been described whereby Triclosan is formed by treating 2,4,4'-trichloro-2'-methoxydiphenyl ether with anhydrous aluminum chloride, or with hydrobromic acid. This precursor to Triclosan has required the availability of 4-chloro-2-methoxyphenol (4-chloroguaiacol), the preparation of which is cumbersome and expensive. The chlorination of guaiacol (2-methoxyphenol) generates large amounts of acidic wastes. Moreover it produces, along with the desired compound, several other chlorinated products which must be removed by meticulous fractional distillation in vacuum.

THE INVENTION

The present invention comprises a process for the synthesis of 2,4,4'-trichloro-2'-methoxydiphenyl ether which does not require 4-chloro-2-methoxyphenol (4 chloroguiacol) as an intermediate.

This is accomplished by starting with the readily and inexpensively available 2,4,4'-trichloro-2-nitrodiphenyl ether, reducing this to the corresponding 2,4,4'-trichloro-2'-aminodiphenyl ether, which is then subjected to a reaction with cupric bromide and an alkyl nitrite to yield 2,4,4'-trichloro-2'-bromodiphenyl ether. Reacting this bromo-compound with sodium methylate yields the desired Triclosan intermediate, 2,4,4'-trichloro-2'-methoxydiphenyl ehter.

The latter two reactions are depicted as follows:

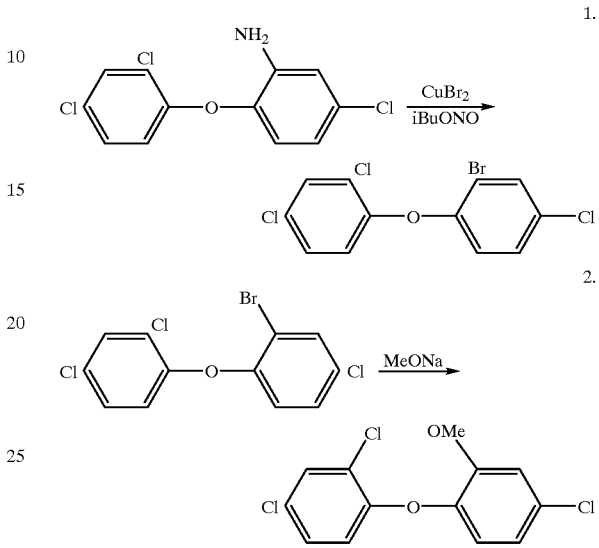

EXAMPLE 1

A.) 28.8 g. 2,4,4'-trichloro-2'-aminodiphenyl ether and 22 g. cupric bromide were added to 150 ml. acetone and the solution was cooled with stirring to 10° C. Then, over 30 min. with vigorous agitation and sufficient cooling to maintain a reaction temperature of 5°–10° C., 15 g. of isobutyl nitrite was added. After an additional 30 min. at 5°–10° C. the solvents were distilled off to near dryness and 40 g. of 40% aqueous hydrobromic acid was added with 100 ml. water and the mixture was stirred at 100° C. for 30 min. The crystallized product was separated from the formed aqueous solution of cupric bromide.

The yield of 2,4,4'-trichloro-2'-bromodiphenyl ether was 33.5 g., N.P. 65° C.

Calculated for Bromine, 22.8% found 22.2%.

B.) 25 g. 2,4,4'-trichloro-2'-bromodiphenyl ether, 25 ml. dimethylformamide, 6 g. sodium methylate are mixed and 1.1 g. cuprous chloride is introduced into the mixture, which is then stirred at 135° C. for five hours. A light vacuum is then applied and the dimethylformamide is distilled off. The residue is mixed with 100 ml. water, then heated, with stirring, to 80° C. and adusted to pH 3 to 4 with 10% aqueous hydrochloric acid. After settling, the product, 2,4,4'-trichloro-2'methoxydiphenyl ether is separated as an oil.

I claim:

1. A process for producing 2,4,4'-trichloro-2'-methoxydiphenyl ether by reacting 2,4,4'-trichloro-2'-bromodiphenyl ether with sodium methylate.

2. 2,4,4'-trichloro-2'-bromodiphenyl ether.

* * * * *